United States Patent [19]

Gross

[11] Patent Number: 5,052,795

[45] Date of Patent: Oct. 1, 1991

[54] MEASURING OPHTHALMOSCOPE AND OPHTHALMOSCOPIC PROCEDURE

[76] Inventor: Peter G. Gross, 714 Oxford Rd., Bala Cynwyd, Pa. 19004

[21] Appl. No.: 324,178

[22] Filed: Mar. 16, 1989

[51] Int. Cl.$^5$ .............................................. A61B 3/10
[52] U.S. Cl. ................................... 351/218; 351/205
[58] Field of Search ............... 351/205, 206, 218, 216, 351/217

[56] References Cited

U.S. PATENT DOCUMENTS 2,370,514  2/1945  Arnesen ............................. 351/218
2,444,172  6/1948  Silverstein ............................ 351/218

Primary Examiner—Rodney B. Bovernick

[57] ABSTRACT

An ophthalmoscopic procedure and ophthalmoscope for quantitative measurement of fundus structures and, in particular, the area of neuroretinal rim are disclosed. Using an ophthalmoscope, a diverging beam of light is projected at a selected fundus structure of the eye being examined. The angle of divergence of the beam is determined from which the light spot size is calculated. A comparison of the light spot and fundus structures is made to measure the fundus structure.

20 Claims, 5 Drawing Sheets

MEASURING OPHTHALMOSCOPE AND OPHTHALMOSCOPIC PROCEDURE

This application relates to the examination of the eye and, in particular, ophthalmoscopes and ophthalmoscopic procedures.

BACKGROUND OF THE INVENTION

Ophthalmoscopes are well known instruments used for eye examinations. A direct ophthalmoscope is a device which has an aperture which defines a line of sight and means for projecting a narrow beam of light in substantial alignment with the line of sight for illumination. The light is directed through the pupil of the eye so that the interior and, in particular the fundus of the eye may be examined.

Typically, a direct ophthalmoscopic procedure includes cyclopleging the eye to dilate the pupil for better viewing. The examiner then directs the projected light beam through the pupil and peers through the peephole into the examinee's eye. Generally, direct ophthalmoscopes include a plurality of lenses which may be rotated or otherwise positioned in the path of the peephole line of sight to focus and/or magnify the interior surface of the eye which is being examined. Some direct ophthalmoscopes provide means for varying the size and intensity of luminosity of the light to adjust the illumination of the interior of the eye to the examiner's preference.

One fundus structure which is typically examined is the optic disc, the structure formed where the optic nerve connects to the eye. Generally the optic disc includes an optic cup and the relative size of the optic disc and cup are easily observed. Conditions such as megalopapilla disc (a gross enlargement of the disc) and hypoplastic disc (an exaggerated diminished disc size) are readily determined through conventional direct ophthalmoscopic examination. Additionally, a skilled examiner can determine through observation the ratio in size between the optic disc and optic cup in order to obtain the relative size of the area of neuroretinal rim which is the area of the disc surrounding the cup.

Other procedures have been developed to obtain a relative measurement of the optic disc and other fundus structures through the use of a retinal graticule. This procedure entails the projection of a grid onto the fundus of the eye and counting the number of squares of the grid occupied by the fundus. The procedure is repeated in subsequent examinations to denote any relative change in the size of the optical disc based on the difference in number of grid sections observed in the first and subsequent examinations.

Grid projection has been accomplished by mounting a slide within the path of the light beam on an adjustable arm and positioning the slide to focus the grid on the fundus. Although research has been done in the calculation of the actual size of the grid squares projected, this procedure has not generally been used to determine a quantitative measurement of the diameter and/or area of the optic disc or other fundus structures. See Morgan, O. G., "A Retinal Graticule", *British Journal of Ophthalmology*, v.11, p. 339, 1927.

One problem in attempting to quantitatively measure fundus structures using grid projection is the fact that the fundus is not flat and the grids cannot be focused over the entire surface. Another apparent problem of quantitatively measuring fundus structures through direct ophthalmoscopic examination is the fact that the eye being examined is a lens and eyes generally vary in size and optic power.

Conventionally, where a quantitative measurement of the optic disc and, in particular, the area of neuroretinal rim is desired, stereoscopic instruments and procedures are used. Such methods entail the need for trained specialists and specialized equipment to achieve an accurate measurement of the desired fundus structure. One known method involves stereoscopic photography; another involves stereoscopic video recording of the fundus, such as with an Optic Nerve Head Analyzer by Rodenstock. Both methods are time consuming and expensive. Accordingly, it is desirable to provide an ophthalmoscopic procedure and ophthalmoscope to obtain a quantitative measurement of fundus structures.

SUMMARY AND OBJECTS OF THE INVENTION

The present invention provides an ophthalmoscopic procedure and ophthalmoscope for quantitative measurement of fundus structures and, in particular, the area of neuroretinal rim. Using an ophthalmoscope, a diverging beam of light is projected at a selected fundus structure of the eye being examined. The angle of divergence of the beam is determined from which the light spot size is calculated. A comparison of the light spot and fundus structures is made to measure the fundus structure.

The invention includes the recognition that the dimension of the projected light spot can be calculated to within approximately ±.07 mm where the projection of the beam is within ±10 mm of the anterior focal distance from the anterior principal plane of the eye using the equation $S = 2f \tan(\alpha/2)$ where S is the diameter of the light spot, is the anterior focal distance and $\alpha$ is the angle of divergence of the light beam. The f term may be based on a statistical measure such as the Gullstrand average of 17.055 mm. Where more precision is needed, f is determined based on the refraction and axial length of the eye being examined which are obtained through conventional methods such as utilizing ultrasonic axial scanning.

It is an object of the invention to provide an ophthalmoscopic procedure for measuring fundus structures by comparing a projected light spot to the fundus structure for either direct coincidence or relative ratio of size between the light spot and the measured structure.

It is also an object of the invention to provide an ophthalmoscope which projects a diverging beam of light and provides a measurement of the angle of divergence to facilitate its use as a measuring apparatus.

It is a further object of the invention to provide a calibrated ophthalmoscope which varies the angle of divergence of the directed beam to facilitate the measurement of fundus structures by matching the light spot in size to the fundus structure being measured.

Other objects and advantages of the present invention will become apparent from the following description of a presently preferred embodiment of the invention.

DETAILED DESCRIPTION OF THE PREFERRED EMBODIMENT

Figure 1:
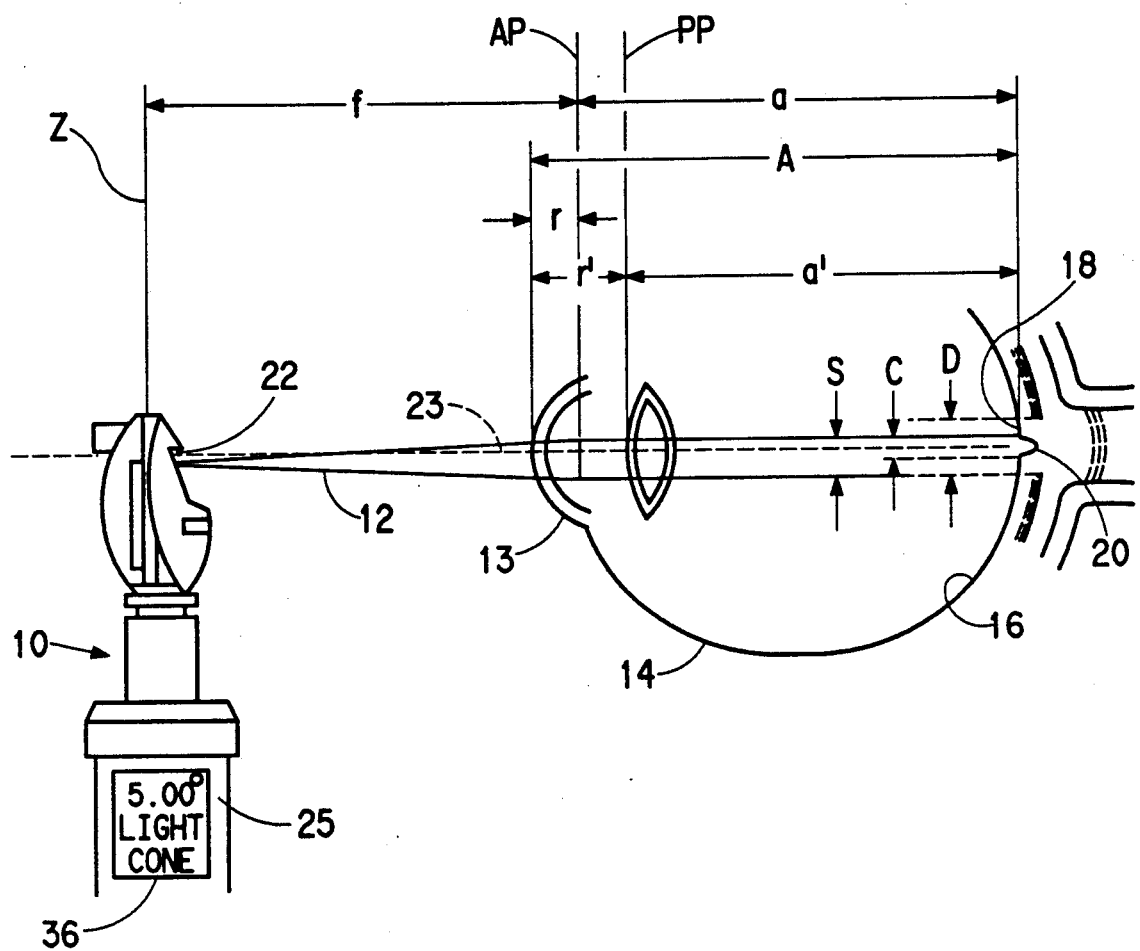
FIG. 1 is an elevation view of an ophthalmoscope made in accordance with the teachings of the present invention projecting a beam of light into an eye which is schematically illustrated.
Figure 2:
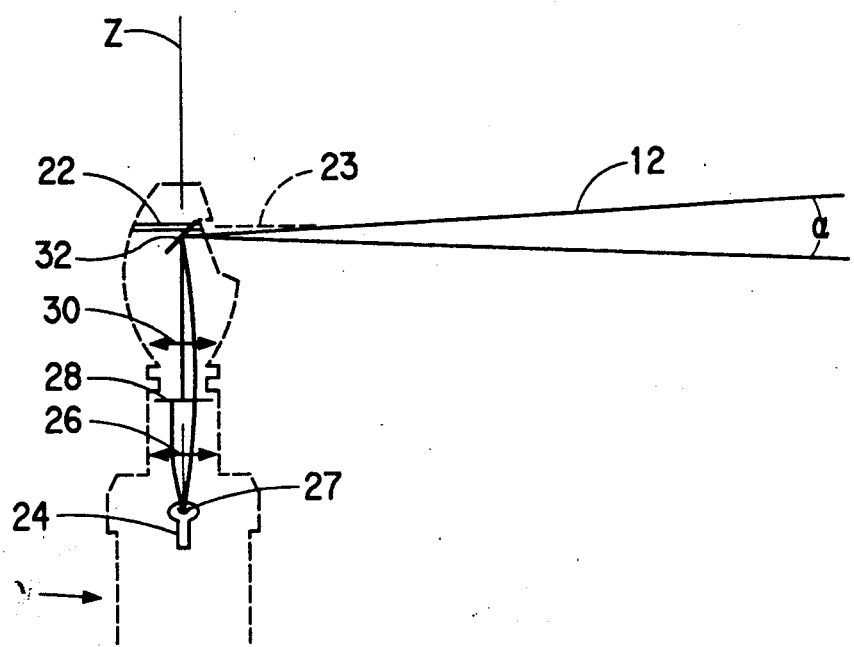
FIG. 2 is a schematic diagram of the optical elements of the ophthalmoscope shown is FIG. 1.

Referring to FIGS. 1 and 2, there is shown ophthalmoscope 10 directing a diverging beam of light 12 having an angle of divergence $\alpha$ through the cornea 13 of an eye 14 to project a light spot having a diameter S on the fundus 16 of the eye 14. The light spot is shown directed onto the optic disc 18 which has a diameter D and the optic cup 20 within the disc 18 which has a diameter C.

The ophthalmoscope 10 includes a peephole 22 through which the examiner observes the fundus 16 along a line of sight 23 which is illuminated by the light beam 12. The peephole may be associated with multiple and/or adjustable lenses (not shown) to focus the vision of the examiner on the observed fundus; such lenses are well known in the art.

As schematically shown in FIG. 2, the light beam 12 emanates from a light source 24 within the handle 25 of the ophthalmoscope 10. Light from the light source travels along a vertical axis Z through a first converging lens 26 having its focus proximate the light emitting element 27 of the light source 24, passes through a selectively sized diaphragm 28 which determines the shape and size of the beam, and then through a second converging lens 30 which focuses the beam on to a reflecting member 32 such as a mirror or a prism.

The reflecting member 32 is positioned at a 45° angle so that the beam 12 is directed orthogonally outwardly from the vertical axis Z of the ophthalmoscope 10. The beam, having been convergently focused onto the reflecting member 32 by lens 30, diverges outwardly in beam 12 of a selected size and shape as determined by diaphragm 28.

The measuring ophthalmoscope 10 of the present invention includes indicating means 36 which provides the examiner with a measurement corresponding to the degree of divergence of the light beam from the reflecting member 32. The indicator means must provide a measurement corresponding to the degree of divergence $\alpha$ with an accuracy of at least 0.5, but preferably the measurement provided is with an accuracy of at least 0.01°. The measurement may be expressed in terms of the light spot dimension calculated as discussed below or any other corresponding measurement of $\alpha$. For example, the measurement may be the diameter of the light spot in millimeters or the area of the light spot in square millimeters.

The eye 14, being a lens system, has a theoretical anterior principal plane AP and a corresponding anterior focal distance f. The location of the anterior principal plane AP and the anterior focal distance vary from eye to eye. FIG. 1 depicts light beam 12 diverging from a point exactly the anterior focal distance f from the theoretical anterior principal plane AP of the eye 14. Accordingly, in accordance with the principles of optics, the diverging beam 12 becomes a beam of parallel light when it passes the anterior principal plane AP and the diameter of the light beam becomes constant. Thus, after passing through the anterior principal plane, the beam diameter is equal to the diameter S of the light spot projected on the fundus.

Figure 3:
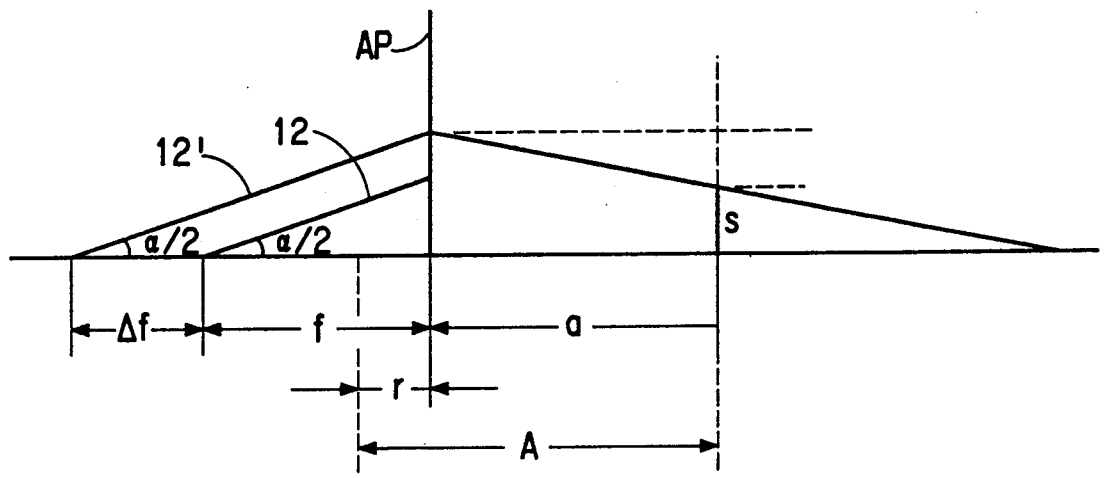
FIG. 3 is a diagram of the half angle ray analysis of the light projected by the ophthalmoscope depicted in FIG. 1.

As shown in the half-ray diagram shown in FIG. 3, the radius of the light beam 12 after it passes the anterior principal plane is equal to f tan($\alpha$/2). Hence, the diameter S of the light spot is a function of the theoretical anterior focal distance f and the angle of divergence $\alpha$ as follows:

$$S = 2f\tan(\alpha/2)$$

Figure 4:
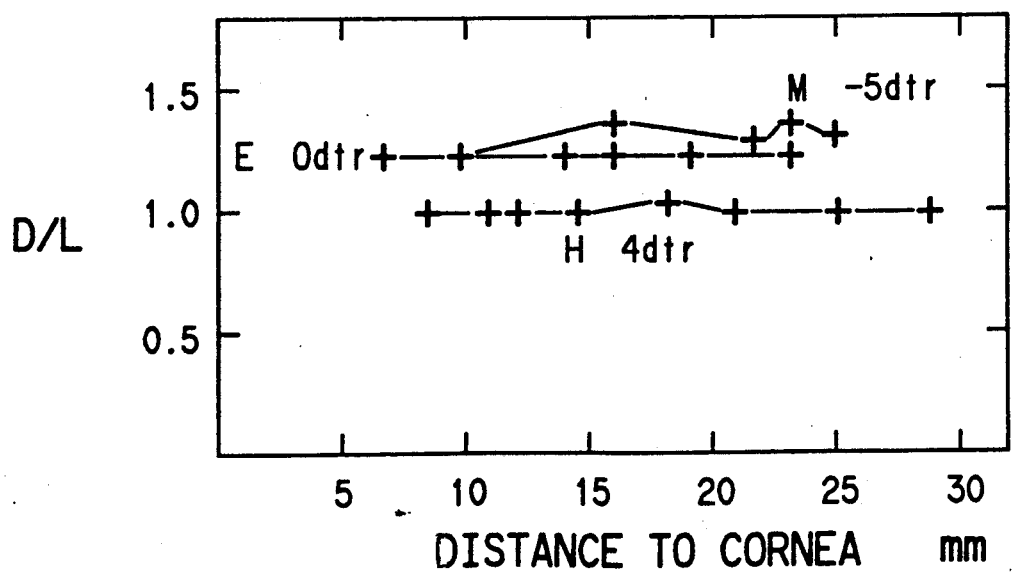
FIG. 4 is a table reflecting observational data of the light spot projected by the ophthalmoscope with respect to three different eyes.

Through observation and analysis it has been discovered that this relationship provides an accurate measure of the light spot even if the ophthalmoscope is not positioned precisely at the focal distance f from the theoretical anterior principal plane AP. In fact, the calculated size of the light spot does not significantly vary over distances from 5 to 30 mm from the cornea. FIG. 4 shows a plot of the optic disc to light spot size ratio for three different eyes at various distances from the respective corneas. One eye was myopic of $-5$ diopters; the second was emmetropic; and the third eye was hyperoptic of $+4$ diopters. The flat curves indicate no substantial change in the dimension of the light spot since the respective optic discs provide a reference of constant size.

Figure 5A:
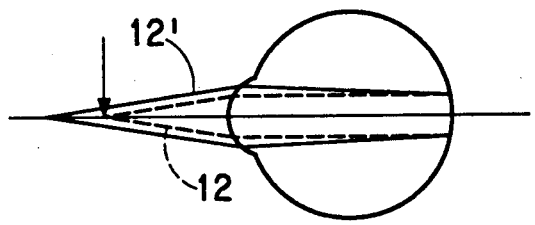
FIGS. 5a and 5b are schematic diagrams of the light beam projected by the ophthalmoscope shown in FIG. 1 from a distance beyond (FIG. 5a) and a distance within (FIG. 5b) the interior focal distance.
Figure 5B:
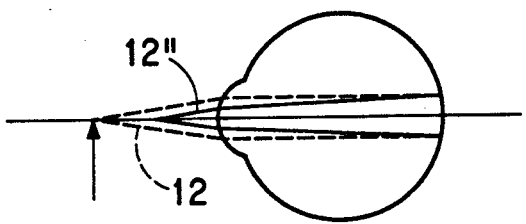

This phenomena is illustrated with respect to FIGS. 5a and 5b. FIG. 5a diagrammatically illustrates the path of a light beam 12' which emanates from a point greater than the focal distance f from the theoretical anterior principal plane; FIG. 5b diagrammatically illustrates the path of a diverging a light beam 12" which emanates from a point less than the focal distance f from the theoretical anterior principal plane.

A mathematical analysis of this phenomena is illustrated in FIG. 3 with respect to light beam 12'. A light beam 12' which emanates from a distance f+^f from the theoretical anterior principal plane will converge (or diverge if ^f is negative) after passing through the theoretical anterior principal plane. The radius s and diameter S of the light spot on the fundus can be determined from the expression:

$$s = f\tan(\alpha/2)\,(1 + [(^{\wedge}f/f)\,(a-n'f)/(n'f)])$$

$$S = 2s = 2f\tan(\alpha/2)\,(1 + [(^{\wedge}f/f)\,(a-n'f)/(n'f)])$$

where
  f plus ^f is the distance at which the diverging beam emanates from the theoretical anterior principal plane;
  $\alpha$ is the degree of divergence of the light beam;

n' is the index of refraction of the eye; and a is the distance between the anterior principal plane and the fundus.

In consideration of average statistical values, however, this exact formula can be greatly reduced. Statistical studies done by Gullstrand show that the theoretical anterior focal length of the eye is typically 17.05 mm and 15.70 mm in front of the cornea since the distance r between the cornea and the theoretical anterior focal principal plane is typically 1.35 mm. The Gullstrand value of average refractive index n' is 1.336 for his reduced skematic eye of 58.46 diopters of refractive power.

Measurements for 1,000 eyes examined by Stenstrom are summarized by A. Linksz, *Physiology of the Eye*, v.1., Grune & Stratton, New York 1950. The bell-shaped distribution has a mean value of 58.13 diopters and a standard deviation of 1.5 diopters. Therefore, if an eye is assumed to have the average total refracting power (or average anterior focal length), then the probability is 70% that the assumption has less than 1.5% error, and the probability is 95% that the assumption has less than 3.0% error.

The term $[(\wedge f/f) (a-n'f)/(n'f)]$ is zero or very near to zero for the two reasons. First, $\wedge f/f$ is zero when the ophthalmoscope is at the anterior focal point and only $\pm 0.5$ when the focal point is missed by $\pm 8$ mm. Second, $(a-n'f)/(n'f)$ is very close to zero for 99% of all eyes, since this is just another way of saying that the retina is very close to the posterior focal point in most eyes, i.e., (n'f) is the posterior focal distance and $(a-n'f)$ is the algebraic difference between the position of the retina and the posterior focal point. Usually, this difference is only on the order of $\pm 1$ mm for a refractive error of $\pm 3$ diopters. Since (n'f) is typically (1.336) (17.055)=22.785, and since Stenstrom's mean axial length of 23.92 mm implies a mean value for this reduced axial length of 23.92−1.35=22.57 mm, the expected mean value of $[(\wedge f/f) (a-n'f)/(n'f)] = (22.57-22.785)/22.785 = -0.01$. Furthermore, this distribution is peaked around the mean much more narrowly than a bell-shaped curve. Thus, the formula for all calculations of spot diameter within approximately $\pm 10$ mm of the anterior focal distance f is reduced to:

$$S = 2f \tan(\alpha/2)$$

This formula reflects that a light beam projected at a constant angle will produce the same size spot whether the ophthalmoscope is 5 mm or 30 mm of the cornea. Statistically, the beam will remain a constant size within $\pm 3\%$ in 95% of clinical cases. Moreover, should an exception to the general rule occur, the examiner may detect such an exception through observing the size of the light spot at varying distances from the cornea. Conversely, if the observed light spot size does not vary, the full weight can be accorded to the measurements obtained through the ophthalmoscopic measuring procedure.

While f may be assumed to be Gullstrand's average of 17.05 mm, a more precise measurement of the light spot is obtained through calculating the actual anterior focal distance f for the eye being examined. This can be done through measurement of the axial length A and refractive error P of the eye being examined. Axial length can be determined through conventional axial ultrasonic scanning methods; refractive error is also easily obtained through conventional methods.

Given that a cycloplegic or equivalent refraction has been carried out, the vergence of a ray from infinity traversing appropriate spectacles of dioptic power P at vertex distance v.d. and imaged onto the retina of a reduced eye whose principal plane is a distance r' behind the cornea will obey the simple-lens relation:

$$(1000/P - v.d. - r')^{-1} (f)^{-1} = n' (A - r')^{-1}$$

The refractive error P is positive for hyperopes and negative for myopes; for emmetropes P=O and the first term in the equation is zero.

The best value of r' is obtained by adopting for the principal plane of the reduced eye the position of the posterior principal plane PP of Gullstrand's average schematic eye. (Even after the spectacle refraction the rays incident on the eye are nearly of zero vergence when compared to their vergence posterior to the second principal plane, i.e., most of the power of the eye, for objects at infinity, is exercised near the posterior principal plane.) r' is taken as the distance 1.35+0.25 mm behind the cornea, the second term being the separation of the two principal planes AP, PP. The value r' = 1.6 mm is therefore adopted for any normal eye, since the complication in trying to determine r' precisely for an individual eye is not worth the gain in accuracy. For example, even a rather unlikely large change in r' of 1 mm will typically introduce only a 4% error (1:24). The traditional value n' = 1.336 is probably accurate to 2% or better, so as a practical course one may adopt r' = 1.6 mm and n' = 1.34 for everyone as constants.

Defining an augmented vertex distance V.D. = v.d. + r' and noting that the distance between the fundus and the posterior principle plane a' = A − r', one obtains:

$$f = a'/[n' - a'/(1000/P - V.D.)].$$

From this equation for the anterior focal length one may see that for the refractive error P in the range of −5 to +4 diopters, with a typical V.D.=15 mm, one has $$f = a'/n' = (A - r')/n'$$

to an accuracy of better than 90%, suggesting that the statistical distributions of f and a will be approximately equally sharply peaked.

The total variation of f is obtained by logarithmic differentiation, which gives:

$$df/f = [(da'/a') \\ (n'f/a')] + [(dP/P)f/(1000/P - 2V.D. + (V.D.)2P/1000)]$$

Note that the coefficient of da'/a' is of order 1, while the coefficient of dP/P is of order 0.01 to 0.1. This shows more explicitly why the distributions of f and a' will be approximately equally narrowly peaked. Thus, for random patient sampling the distribution of anterior focal lengths will be similar to the distribution of axial lengths.

The recognition of the fact that the size of the light spot S projected on the fundus can be accurately calculated to within approximately $\pm 0.07$ mm from the angle of divergence of the light beam 12 projected from the ophthalmoscope 10, transforms the ophthalmoscope from an examination instrument into a measuring instrument. Measurement of fundus structures can be performed either by comparison of a light spot of a fixed dimension to the measured structure or by varying the light spot until it coincides with the dimension of the structure being measured.

Where the diaphragm 28 is non-variable, the ophthalmoscope is labeled to indicate the fixed degree of divergence $\alpha$ such as shown in FIG. 1 where the fixed diaphragm causes the ophthalmoscope 10 to project a right conical beam having a 5.00° angle of divergence. Using Gullstrand's average of 17.05 mm, the diameter of the light spot projected on the fundus is 1.49 mm (=2 (17.05) tan(5.00/2)).

Figure 6A:
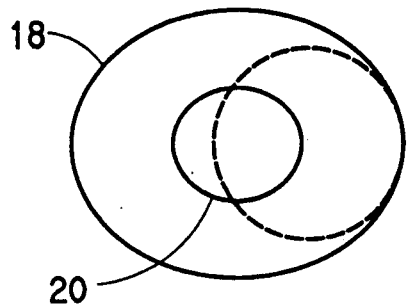
FIGS. 6a and 6b are schematic diagrams depicting the measurement of the optic disc relative to the light spot projected by the ophthalmoscope shown is FIG. 1.
Figure 6B:
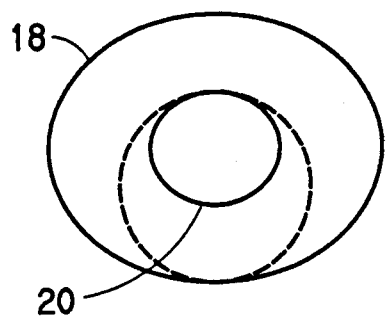
Figure 7:
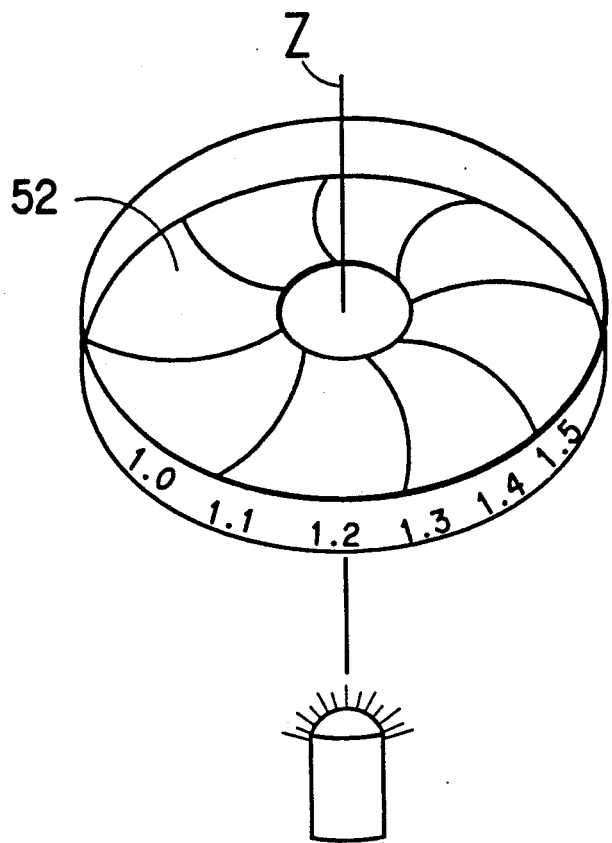
FIG. 7 depicts an alternate embodiment for the diaphragm of the ophthalmoscope shown is FIG. 1.

With reference to FIGS. 6a and 6b, the area of neuroretinal rim which lies within the optic disc 18 outside of the optic cup 20 can be measured by comparison to a light spot which is of known size. As noted above, skilled examiners are readily able to determine the optic disc to optic cup size ratio through observation. Typically this is done through assuming an elliptical shape of the cup and disc and determining the cup-to-disc vertical axial ratio and cup-to-disc horizontal axial ratio. For determining a quantitative measurement, the disc-to-spot ratios between the diameter of the light spot and the horizontal disc axis (FIG. 6a) and between the diameter of the light spot and the vertical disc axis (FIG. 6B) are determined by observation (or for greater precision by photographing the fundus and measuring the spot and disc from the photograph). Knowing the diameter of the light spot, geometric calculation of the area of neuroretinal rim is easily determined using these ratios The usefulness of the ophthalmoscope 10 as a measuring device can be augmented through replacing the fixed diaphragm 28 with a variable diaphragm such as one of the alternate embodiments depicted in FIGS. 7, 8 and 9. For example, FIG. 7 illustrates an infinitely variable iris diaphragm 52 may be employed which is calibrated to reflect changes in the divergence angle $\alpha$ of 0.01° over a range of $\alpha$ from 1.00 to 15.00°.

Figure 8:
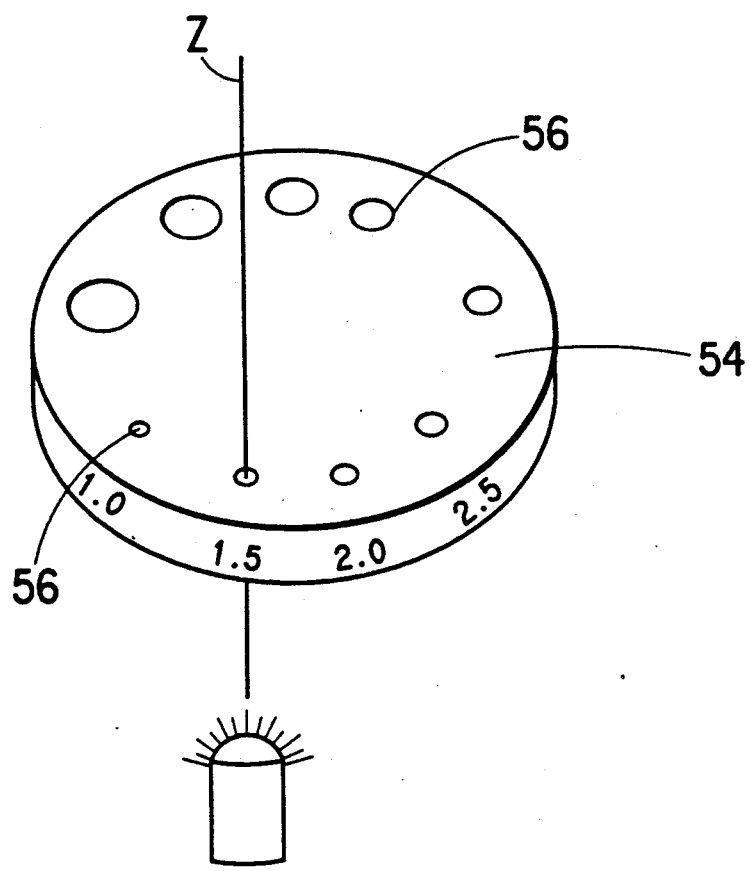
FIG. 8 depicts a second alternate embodiment for the diaphragm of the ophthalmoscope shown in FIG. 1.

Alternately, as depicted in FIG. 8, the diaphragm may comprise a disc 54 which is rotatable to position selectively sized apertures 56 within the Z axis of the light beam of the ophthalmoscope 10. Disc 54 being calibrated and/or associated with calibration means to reflect the measurement of the angle produced by the respective apertures 56 with the desired degree of precision.

Figure 9:
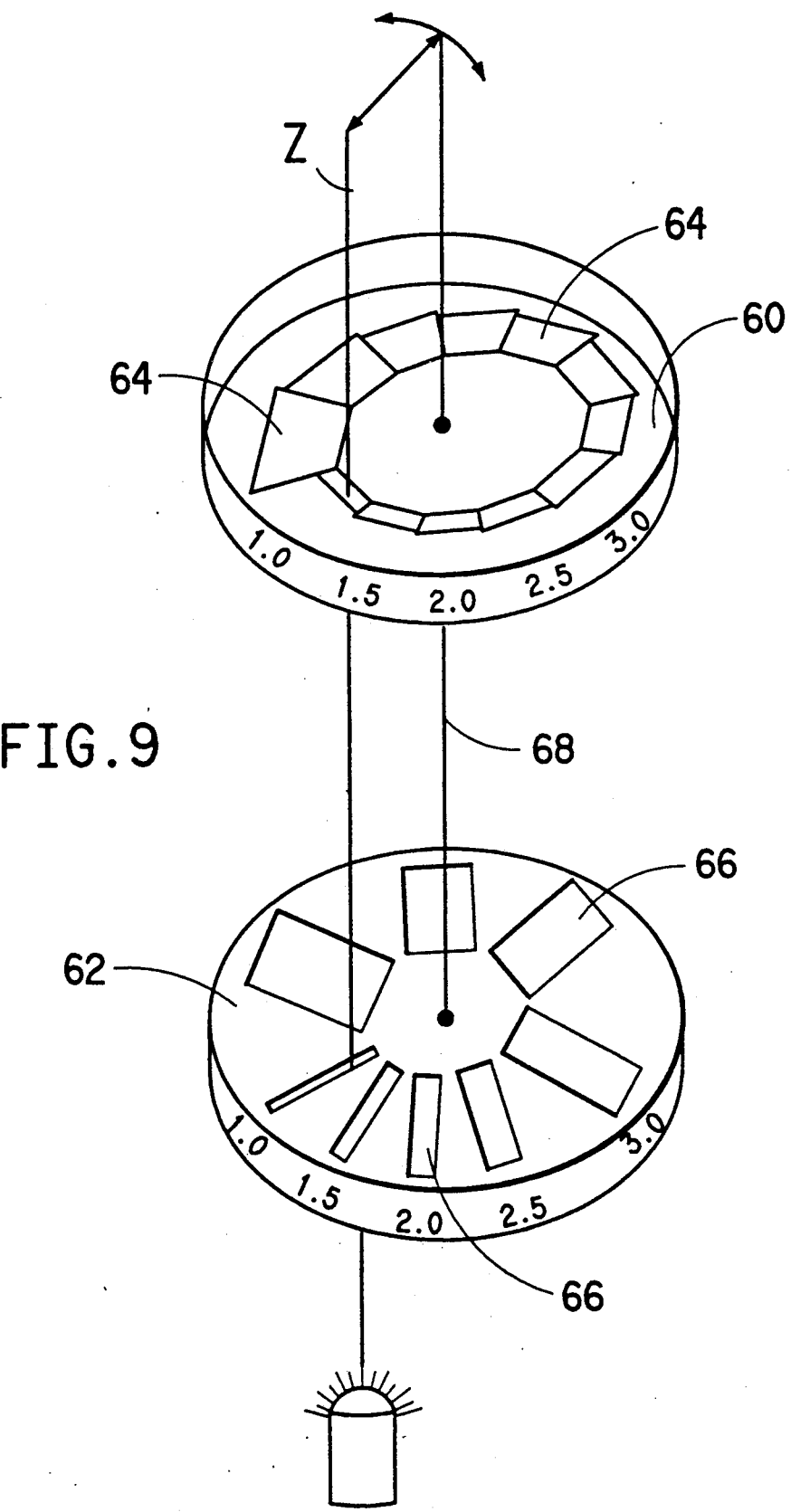
FIG. 9 is an exploded view of a third alternate embodiment of a diaphragm for the ophthalmos shown in FIG. 1.

As shown in FIG. 9, a third alternate diaphragm comprises an upper disc 60 and lower disc 62. The upper disc has a concentric array of rectangular slits 64 of graduated sizes and the lower disc has a radial array of graduated size slits 66. The discs are mounted for rotation about a common axis 68 such that the respective slits 64, 66 can be positioned within the vertical Z axis of the light beam within the ophthalmoscope handle. The slits cause the projected beam to be pyramidical in shape and the corresponding light spot to be rectangular. The discs are calibrated to provide the degree of divergence with respect to each opposing pair of pyramidal sides, respectively.

Figure 10:
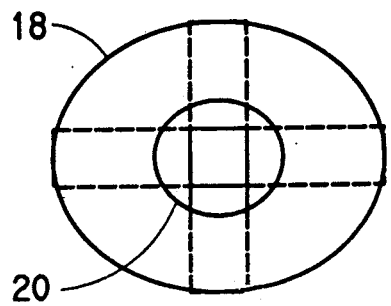
FIG. 10 is schematic view illustrating the measurement of the optic disc utilizing an ophthalmoscope equipped with the diaphragm shown in FIG. 9

As shown in FIG. 10, the light beam may be directed at the center of the optic disc and expanded in the vertical direction (shown in phantom) to determine the vertical diameter of the disc; then, after resetting the vertical dial control to its smallest setting, adjusting the horizontal spot to measure the horizontal axis of the disc (shown in phantom) through coincidence with the spot. The optic cup 20 can also be measured by the same procedure.

Diaphragm discs 60 and 62 may be mounted such that their axis of rotation may be displaced accurately about the Z axis of the light beam within the ophthalmoscope 10. Such mounting would be to effect a rotational movement of the light spot to facilitate measuring fundus structures without moving the handle of the ophthalmoscope. Many different arrangements are possible; however, one other is useful to mention, namely, wherein different lenses of different optical power may be rotated into the light beam either before or after the light is reflected at the mirror or prism located at the peephole of the instrument. This is arranged so as to affect only the light beam (and thereby the light beam angle $\alpha$) and not the line of sight.

Although a presently preferred embodiment of the invention has been disclosed, it is well within the scope of the invention to utilize computer means either directly or indirectly associated with the ophthalmoscope to perform the various size computations and measurements. Calibration of the ophthalmoscope may be done either analogically or through sufficiently accurate digital means which could, for example, include a microprocessor in the handle of the ophthalmoscope. Likewise, the utility of the measuring ophthalmoscope is not limited to measuring the optic disc but may be used to measure lesions, tumors or other fundus structures.

I claim:

1. An ophthalmoscopic procedure for measuring fundus structures within an eye comprising:
   projecting a divergent beam of light on the fundus of the eye from within 5–30 mm of the eyes cornea such that a spot of light is projected on the structure to be measured;
   varying the degree of divergence of light beam such that the light spot coincides with the perimeter of the structure being measured; and
   determining the degree of divergence of said light beam when the actual size of said light spot coincides with the perimeter of said structure.

2. An ophthalmoscopic procedure for measuring fundus structures within an eye according to claim 1 further comprising:
   calculating the size of said structure as a function of said determined degree of divergence based on the formula: $S = 2f \tan(\alpha/2)$ where S is the linear measurement of the spot size, f is the eye's anterior focal length and is the degree of divergence of said light beam.

3. An ophthalmoscopic procedure for measuring fundus structures within an eye according to claim 2 further comprising:
   measuring the axial length of the eye and calculating f based on said measurement.

4. An ophthalmoscopic procedure for measuring fundus structures within an eye according to claim 1 further comprising:
   performing said projecting, varying and determining steps with respect to both the optic disk and optic cup; and
   calculating the size of the area of neuroretinal rim as a function of said degrees of divergence determined with respect to the optic disk and optic cup, respectively.

5. An ophthalmoscopic procedure for measuring fundus structures within an eye comprising:
projecting a divergent beam of light on the fundus of the eye from within 5-30 mm of the eyes cornea such that a spot of light is projected on the structure to be measured;
determining the degree of divergence of said light beam; and
comparing the size of said light spot with the structure being measured to determine the relative size of the structure to the light spot.

6. An ophthalmoscopic procedure for measuring fundus structures within an eye according to claim 5 further comprising:
calculating the size of said structure as a function of said determined degree of divergence based on the formula: $S = 2f \tan(\alpha/2)$ where S is the linear measurement of the spot size, f is the eye's anterior focal length and $\alpha$ is the degree of divergence of said light beam.

7. An ophthalmoscopic procedure for measuring fundus structures within an eye according to claim 6 further comprising:
measuring the axial length of the eye and calculating f based on said measurement.

8. An ophthalmoscopic procedure for measuring fundus structures within an eye according to claim 5 further comprising:
performing said projecting, varying and determining steps with respect to both the optic disk and optic cup; and
calculating the size of the area of neuroretinal rim as a function of said degrees of divergence determined with respect to the optic disk and optic cup, respectively.

9. An ophthalmoscopic procedure for measuring fundus structures within an eye according to claim 5 further comprising:
observing the size of the light spot at varying distances from the cornea to determine the weight to be accorded to the measurements obtained through the ophthalmoscopic measuring procedure.

10. A measuring ophthalmoscope comprising:
aperture means for providing a line of sight;
means for projecting a divergent beam of light focused proximate said aperture means and substantially aligned with said line of sight to thereby project a spot of light onto the fundus of an eye which is observable along said line of sight;
means for selectively varying the degree of divergence of said beam of light to correspondingly vary the size of said light spot; and
calibration means associated with said varying means for measuring the degree of divergence of said beam and, accordingly, measuring the actual size of the projected light spot at the fundus.

11. A measuring ophthalmoscope according to claim 10 wherein said calibration means measures the degree of divergence at least to 0.5° accuracy.

12. A measuring ophthalmoscope according to claim 10 wherein said calibration means provides linear measurement to at least 0.1 mm accuracy based on the relationship $S = 2f \tan(\alpha/2)$ where S is the linear measurement of the spot size, f is the eye's anterior focal length and is the degree of divergence of said light beam.

13. A measuring ophthalmoscope according to claim 10 wherein said divergent beam is conical.

14. A measuring ophthalmoscope according to claim 13 wherein said varying means comprises an iris diaphragm.

15. A measuring ophthalmoscope according to claim 10 wherein said divergent beam is pyramidal.

16. A measuring ophthalmoscope according to claim 15 further comprising:
means for independently varying the divergence of the two pair of opposing sides of said pyramidal beam; and
calibration means associated with the respective divergence of each said pair of opposing sides.

17. A measuring ophthalmoscope according to claim 10 wherein said calibration means includes indicator means for indicating the degree of divergence of said beam in degrees with an accuracy of at least 0.1°.

18. A measuring ophthalmoscope according to claim 12 wherein said calibration means includes indicator means for indicating the diameter of the projected light spot in linear measurement.

19. A measuring ophthalmoscope according to claim 12 wherein said calibration means includes indicator means for indicating the area of the projected light spot in square measurement.

20. A measuring ophthalmoscope comprising:
aperture means for providing a line of sight;
means for projecting a divergent beam of light focused proximate said aperture means ad substantially aligned with said line of sight to thereby project a spot of light onto the fundus of an eye which is observable along said line of sight; and
means for varying the angle of divergence of said beam and indicator means for indicating the degree of divergence of said beam with an accuracy of at least 0.1° and, accordingly, for indicating the actual size of the projected light spot at the fundus.

* * * * *